(12) United States Patent
Wong et al.

(10) Patent No.: US 6,459,762 B1
(45) Date of Patent: Oct. 1, 2002

(54) METHOD FOR PRODUCING A RANGE OF THERAPEUTIC RADIATION ENERGY LEVELS

(75) Inventors: James R. Wong, Morristown, NJ (US); Chee-Wai Cheng, Randolph, NJ (US)

(73) Assignee: Ro Inventions I, LLC, Morristown, NJ (US)

(*) Notice: Subject to any disclaimer, the term of this patent is extended or adjusted under 35 U.S.C. 154(b) by 46 days.

(21) Appl. No.: 09/805,536

(22) Filed: Mar. 13, 2001

(51) Int. Cl.[7] .................................................. A61N 5/10
(52) U.S. Cl. ........................................................ 378/65
(58) Field of Search .................................... 378/65, 108

(56) References Cited

U.S. PATENT DOCUMENTS

| | | | | |
|---|---|---|---|---|
| 4,118,653 A | * | 10/1978 | Vaguine ..................... 315/5.41 |
| 4,162,423 A | * | 7/1979 | Tran ........................... 315/5.41 |
| 5,027,818 A | | 7/1991 | Bova et al. .................. 128/653 |
| 5,202,565 A | | 4/1993 | Torii ......................... 250/327.2 |
| 5,216,255 A | | 6/1993 | Weidlich ................. 250/492.3 |
| 5,291,404 A | | 3/1994 | Kurokawa et al. ..... 364/413.26 |
| 5,418,827 A | | 5/1995 | Deasy et al. ................. 378/65 |
| 5,538,494 A | | 7/1996 | Matsuda ........................ 600/1 |
| 5,602,892 A | | 2/1997 | Llacer .......................... 378/65 |
| 5,647,663 A | | 7/1997 | Holmes .................... 128/653.1 |
| 5,661,377 A | * | 8/1997 | Mishin et al. ............... 315/505 |
| 5,663,999 A | | 9/1997 | Siochi ........................... 378/65 |
| 5,668,847 A | | 9/1997 | Hernandez ................... 378/65 |
| 5,880,477 A | | 3/1999 | Perilleux et al. .......... 250/492.3 |
| 6,024,689 A | | 2/2000 | Castle et al. ................... 600/1 |
| 6,038,283 A | | 3/2000 | Carol et al. ................... 378/65 |
| 6,142,925 A | | 11/2000 | Siochi et al. ................... 600/1 |

* cited by examiner

*Primary Examiner*—Robert H. Kim
*Assistant Examiner*—Allen C. Ho
(74) *Attorney, Agent, or Firm*—Duane Morris LLP

(57) ABSTRACT

The present invention provides a method for producing a broad range of therapeutic radiation energy levels with a source of radiation that is operated to produce photons or particles at a first energy that are directed at a treatment site for a predetermined absorbed dose. The linear accelerator is then operated to produce photons or particles at a second energy directed at the treatment site for another predetermined absorbed dose. The appropriate selection of the first and second absorbed doses yields an absorbed dose at the treatment site equivalent to the dose produced by photons having an energy that is intermediate of the first and second energies. Thus, a dual energy linear accelerator may be operated according to the method to yield a continuous range of energies.

26 Claims, 6 Drawing Sheets

METHOD FOR PRODUCING A RANGE OF THERAPEUTIC RADIATION ENERGY LEVELS

FIELD OF THE INVENTION

The present invention generally relates to radiation oncology, and more particularly to methods for oncological treatment with linear accelerators.

BACKGROUND OF THE INVENTION

Radiation-emitting devices are generally known and used for radiation therapy in the treatment of patients. In a typical radiation therapy device, the gantry of a linear accelerator is swivelled around a horizontal axis of rotation in the course of a therapeutic treatment of a patient. The linear accelerator generates a high-energy radiation beam (referred to herein as a "photon beam" or "photons") for use in the therapeutic treatment.

Historically, linear accelerators used in radiation therapy applications have been equipped to provide only a single energy photon beam. In the recent past, however, some linear accelerators have been equipped to provide two different energy beams. The limited number of energies available is a continuing problem for physicians and physicists, since it is not always possible for them to give the most efficacious treatments. For example, the most commonly available dual energy linear accelerator provides six megavolt (MV) photons and either ten or fifteen MV photons. This is a typical combination since, e.g., in the treatment of breast cancer, an irradiation treatment of the whole breast is best accomplished with six MV photons. For tumors located deep within the body, however, the most commonly used energies are ten MV and fifteen MV photons. Of course, there are other tumor sites that are best treated with four MV or eight MV photons. Four MV photons are very effective for the treatment of tumors near the skin surface, while eight MV photons are excellent for the irradiation of larger breasts. Four MV and eight MV photon energies are usually not incorporated in dual energy linear accelerators because they are not needed all the time, and thus are not considered cost effective. Currently, certain manufacturers are attempting to provide linear accelerators with the capability of generating three different photon energies. Such machines, however, will still preclude many other intermediate energies that may be useful.

A therapeutic x-ray beam produced by a linear accelerator is characterized by the amount of energy that will be deposited at a treatment site by that particular x-ray beam. This characterization relates to the depth (usually measured from the surface of the skin) at which the beam's maximum energy is deposited (often referred to in the art as "dmax"). In radiation therapy, the energy deposited by ionizing radiation (absorbed dose) is typically measured in "grays" or "Gy", instead of the traditional unit of measure of absorbed dose, the "rad." It will be understood that a dose of one Gy will deposit one joule of energy per kilogram of matter, and that one rad is equal to 1 one-hundredth of a Gy, or one "cGy." Thus, dmax is often represented in the form of absorbed dose in units of cGy. The absorbed dose depends upon the exposure (time and intensity) as well as the inherent characteristics of the absorbing matter, i.e., density, atomic number, etc.

For example, assuming a ten by ten cm (centimeter) field, a low energy x-ray beam (e.g., six MV) would deposit the maximum energy at one and a half cm from the surface of the skin, while a high energy beam, such as fifteen MV, would deposit the maximum energy at three cm from the surface of the skin. Thus, with a fifteen MV beam, any point closer than three cm to the surface of entry would be less than dmax and any point more than three cm from the surface of entry would also be less than dmax. At locations that are nearer to the surface or further away from the surface than the location of dmax, radiation energy is deposited to a lesser degree and at a lower rate. A significant difference between higher energy beams and lower energy beams is that the higher energy beams are more penetrating. That is, the amount of radiation deposited at a given point (say five cm) beyond the location of dmax is higher for a fifteen MV beam than it is for a six MV beam. Thus, a fifteen MV beam is more effective in treating a deep seated tumor (say fifteen cm from the surface/skin) than a six MV beam.

A standard technique for treating a breast is called "tangential beams." Here the radiation is given by two nearly opposing beams arranged at an angle so that they just skim the chest wall (to minimize radiation exposure to the lungs) but otherwise treat the entire breast. The base of a human breast generally provides the widest separation, (i.e., the greatest transit distance through tissue, sometimes as much as twenty-five cm. With such a wide separation, a more penetrating beam is needed. However, with a fifteen MV beam, which deposits a maximum energy at three cm, the beam may not be treating the breast tissue adequately near the skin surface. However, if a six MV beam is used, it may be more appropriate in covering the breast tissue near the skin surface, but may not be treating the deep tissue adequately.

One solution in the art has been to increase the amount of radiation that is given for each treatment so that the tissue at the center of the base of the breast receives an adequate amount of radiation with a six MV beam. Unfortunately, a consequence of this method is that the tissue near the skin becomes so "hot" (receiving too much radiation) that the breast exhibits significant skin side effects (almost like a severe sun burn). In such a case, an eight MV beam would be more appropriate, since it would treat the breast tissue near the skin appropriately but yet more penetrating than the six MV beam. Unfortunately, eight MV beam machines are not commonly used at healthcare facilities.

Numerous methods and apparatus have been disclosed in the prior art for optimizing radiation therapies. For example, in U.S. Pat. No. 6,038,283, a method and apparatus for determining an optimized radiation beam arrangement for applying radiation to a tumor target volume while minimizing radiation of a structure volume in a patient is disclosed. The method uses an iterative cost function based on a comparison of desired partial volume data, which may be represented by cumulative dose volume histograms and proposed partial volume data for target tumors and tissue structures. This arrangement provides for the delivery of the optimized radiation beam arrangement to the patient by a conformal radiation therapy apparatus.

U.S. Pat. No. 6,142,925 discloses a method and system for increasing resolution of a radiotherapy system to achieve virtual fractional monitor unit radiation delivery. The method identifies a desired treatment dose that exceeds the resolution of a radiation treatment device, and develops a schedule of treatment sessions for delivering the desired treatment dose that produces a combined treatment dose equaling the desired treatment dose without exceeding the resolution within each treatment session.

U.S. Pat. No. 5,880,477, discloses a method and apparatus for real time control of the dose rate of particles or ionizing radiation, especially X-ray radiation, generated from an electron linear gun and applied to polymer resins using an appropriate ionization chamber having planar electrodes placed in the field of particles. The method involves sampling continuously the current for collecting the load between the electrodes. The instantaneous dose rate of the radiation is represented by the collecting current. Using an appropriate shielded conducting system, the collecting current is directed to an amplification and measurement circuit arranged outside of the irradiation zone. The intensities of the current are translated into dose rate values. The does rate values are then processed and/or displayed and/or recorded.

U.S. Pat. No. 5,668,847 discloses a radiation emitting device for therapeutic radiation treatment which adjusts the actual radiation delivered to an object via a radiation beam, and which is dependent on the dimensions of an opening in a plate arrangement provided between a radiation source and an object. In this way, the radiation output has a constant wedge factor over an irradiation field, regardless of the size of the opening. The wedge factor is defined as the ratio between a reference radiation output along a reference axis of the beam with a predetermined physical wedge in the beam path and an actual radiation output of the beam in a substantially lossless beam path.

U.S. Pat. No. 5,647,663 discloses a method of radiation treatment planning for radiation systems providing multiple beams of independently adjustable intensities which limits the iterative beam weight determination to a set of discrete beam weights. This method avoids errors in post-optimization truncation of the beam weights, and decreases the iteration time. Those beams having a greatest effect on the solution are preferentially adjusted and larger changes between discrete values of beam weights are given preference to smaller changes.

U.S. Pat. No. 5,602,892, discloses a method for optimization of radiation therapy planning based on a Dynamically Penalized Likelihood (DLP) algorithm. The target function of the DLP algorithm contains likelihood terms and penalty terms connected to the likelihood terms by a number of dynamically updated penalty coefficients. The method results in a highly uniform dose to the tumor or radiosurgery volume, at the expense of some non-uniformity in the dose delivered to defined sensitive tissues.

U.S. Pat. No. 5,418,827, discloses a radiation therapy apparatus for irradiation of a tumor at 360° about the tumor within a plane. The apparatus determines a distribution of charges in a conductor that would produce a potential energy field matching the desired dose to the tumor in the plane. The fluence of any given ray through the tumor is determined by summing the charges along the ray's path. The distribution includes areas of no irradiation which may require negative fluences. Physically realizable non-negative fluences are obtained by an iterative process of adjusting an input dose map in light of the actual dose produced by the calculated fluences.

U.S. Pat. No. 5,291,404, discloses a radiotherapy treatment planning system for calculating the radiation dose to be absorbed by an object to be irradiated, prior to radiotherapy. The distribution of the contribution output unit provides the distribution of contribution showing the contribution rates of scattered beam or electron beam to an observational point in each point of the object to be irradiated. An arithmetic unit calculates the absorbed dose of the observational point due to the scattered beam or the absorbed dose due to the electron beam, by summing up each contribution rate multiplied with the electron density at the corresponding point.

U.S. Pat. No. 5,216,255, discloses a system for applying radiation treatment undercomputercontrol. The system has a radiation source which generates a variable intensity radiation beam, and a collimator. The collimator has a plurality of movable plates disposed in the path of the radiation beam and is oriented in a direction perpendicular to the beam axis. The apparatus is capable of actuating the plates independently during the radiation treatment, in response to a first control signal. The beam changes in width when the plates are so actuated. The collimator is rotated in response to a second control signal. The intensity of the radiation beam may be varied as a function of the plate position. A total radiation dosage is applied during two intervals. The first interval precedes the collimator rotation, and the second interval follows the rotation.

U.S. Pat. No. 5,027,818, discloses a technique for computing the doses at various points within the patient's body. In particular, the doses are computed at a relatively high density of points within a fine dose grid and at a relatively low density of points within a coarse dose grid. In that fashion, the user can quickly obtain necessary information about the radiation dose distribution before implementation of a proposed treatment plan. A technique of locating the intersection between the radiation beam and the contour or other surface of the patient is also provided. The method appears well suited for use with a particular structure which allows one to utilize relatively narrow beam widths as a result of great mechanical accuracy.

The foregoing patents are hereby incorporated herein by reference.

Prior art dual energy linear accelerators on the market today typically include a low energy beam (usually six megavolts or "MV") and a higher energy beam (usually a fifteen MV). Obtaining beam energies between six and fifteen MV has been very difficult to achieve, often requiring the purchase of an intermediate energy linear accelerator. The purchase price of a single energy linear accelerator is currently a little more than half the price of a dual energy linear accelerator. Thus, the cost differential between single energy linear accelerators and dual energy linear accelerators is quite significant. This creates a practical economic barrier for most health care facilities. There is a need for a method of providing a large range of energy levels from available linear accelerators.

SUMMARY OF THE INVENTION

The present invention provides a method for producing a broad range of therapeutic radiation energy levels with a source of more than one value of radiation energy, e.g., a dual energy linear accelerator. In one embodiment of the inventive method, a dual energy linear accelerator is operated to produce photons at a first energy that are directed at a treatment site for a first absorbed dose. The linear accelerator is then operated to produce photons at a second energy directed at the treatment site for a second absorbed dose. The appropriate selection of the first and second absorbed doses yields an effective absorbed dose at the treatment site equivalent to the dose produced by photons having an energy that is intermediate of the first and second energies. Alternatively, the appropriate selection of the first and second doses may be presented in the form of dose characteristics (dose distributions) at the treatment site equivalent to the dose characteristics (dose distributions) produced by photons having an energy that is intermediate of the first and second energies. Thus, a four MV and fifteen MV dual energy linear accelerator may be operated according to the method to yield a continuous range of energies, e.g., 4, 5, 6, 7, 8, 9, 10, 11, 12, 13, 14, or 15 MV photons or particles. In another embodiment, an absorbed dose at the treatment site may be produced corresponding to the application of non-integer photon energies.

In another embodiment, a dual energy linear accelerator is operated to produce simultaneously photons at a first energy and photons at a second energy where the ratio of first energy photons to second energy photons is set according to a predetermined proportion. This composite stream of photons is then directed at a treatment site. The appropriate selection of the ratio of first energy photons to second energy photons imparts a photon dose at the treatment site equivalent to the dose produced by photons having an energy that is intermediate of the first and second energies.

In yet another embodiment, a dual energy linear accelerator is operated so as to produce photons at a first energy, which are directed at a treatment site to impart a fraction of a first absorbed dose. This operation is repeated until a whole first absorbed dose has been applied to the treatment site. The dual energy linear accelerator is then operated so as to produce photons at a second energy, which are directed at the treatment site to impart a fraction of a second absorbed dose. This operation is repeated until a whole second absorbed dose has been applied to the treatment site. The first and second whole absorbed doses are selected so as to impart an effective absorbed dose at the treatment site equivalent to an absorbed dose produced by photons having an energy that is intermediate of the first and second energies.

In a further embodiment, a dual energy linear accelerator is operated to produce photons at a first energy that are directed at a treatment site from a first direction to impart a first absorbed dose. The linear accelerator is then operated to produce photons at a second energy directed at the treatment site from a second direction to impart a second absorbed dose. The appropriate selection of the first and second absorbed doses and directions yields an effective absorbed dose at the treatment site equivalent to the dose produced by photons having an energy that is intermediate of the first and second energies.

BRIEF DESCRIPTION OF THE DRAWINGS

These and other features and advantages of the present invention will be more fully disclosed in, or rendered obvious by, the following detailed description of the preferred embodiments of the invention, which are to be considered together with the accompanying drawings wherein like numbers refer to like parts and further wherein.

DETAILED DESCRIPTION OF THE PREFERRED EMBODIMENT

The present invention provides a method for producing a broad range of therapeutic radiation energy levels with a source of radiation, e.g., a dual energy linear accelerator, by mixing the beams to produce dosage characteristics (or energy characteristics or photon distributions) at the treatment site that mimic or closely approximate the dosage characteristics (or energy characteristics or photon distributions) from a beam having characteristics associated with a beam of intermediate energy. The method of the invention is described with reference to a system for delivering photons, e.g., x-ray radiation, to a treatment site of a patient, e.g., a tumor, but it will be understood that the method of the invention may be practiced with any form of radiation beam therapy, i.e., photons or particles, with substantially equal effect. Also, the method of the invention is described with reference to dual energy linear accelerators having specific energy beams available, e.g., four, six, fifteen megavolts, but it will be understood that the method of the invention may be practiced with any combination of energy beams, i.e., energies less than four or greater than 15.

Figure 1:
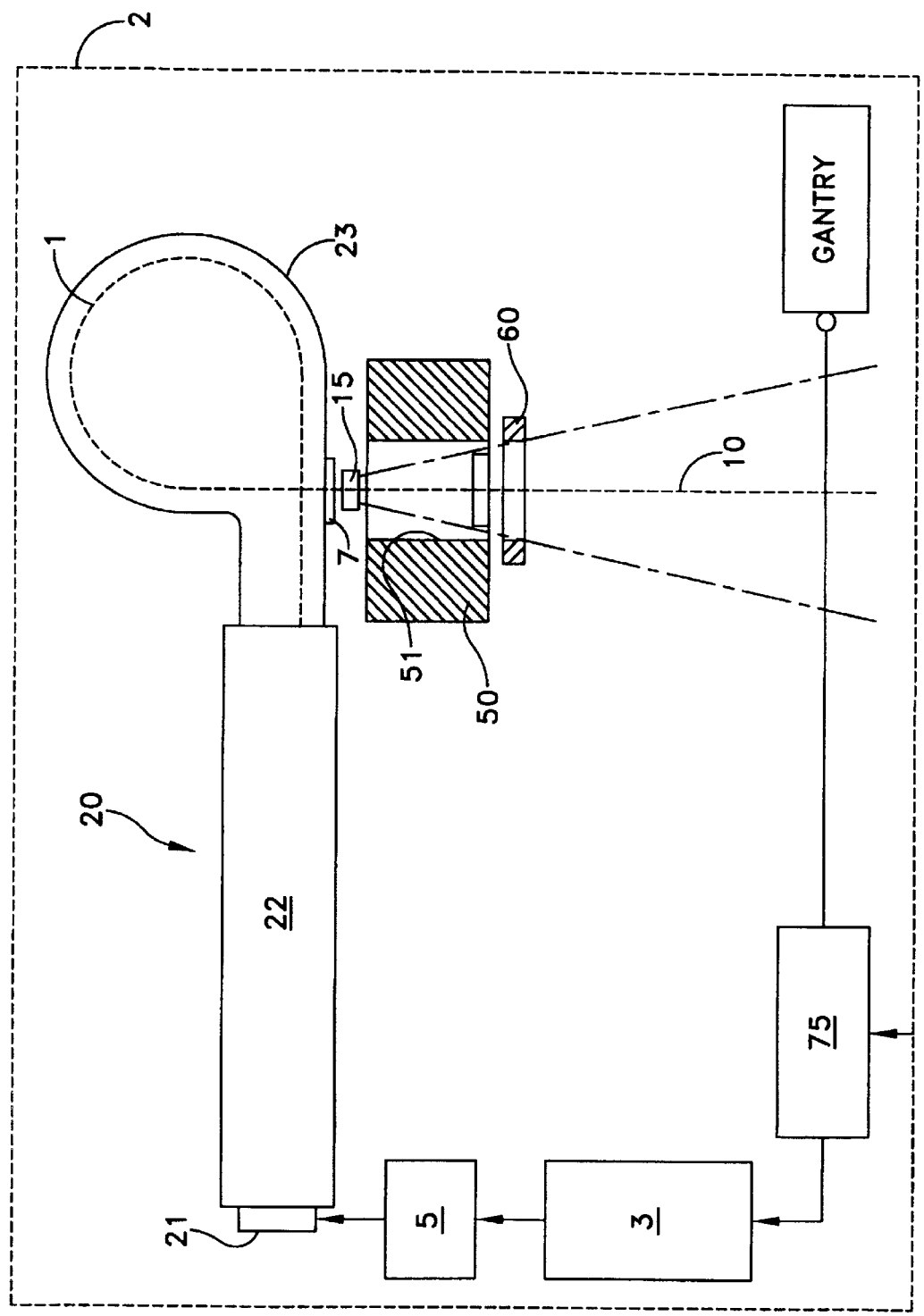
FIG. 1 is a schematic block diagram illustrating portions of a therapeutic radiation beam generation system in a radiation treatment device used in connection with the present invention.
Figure 2:
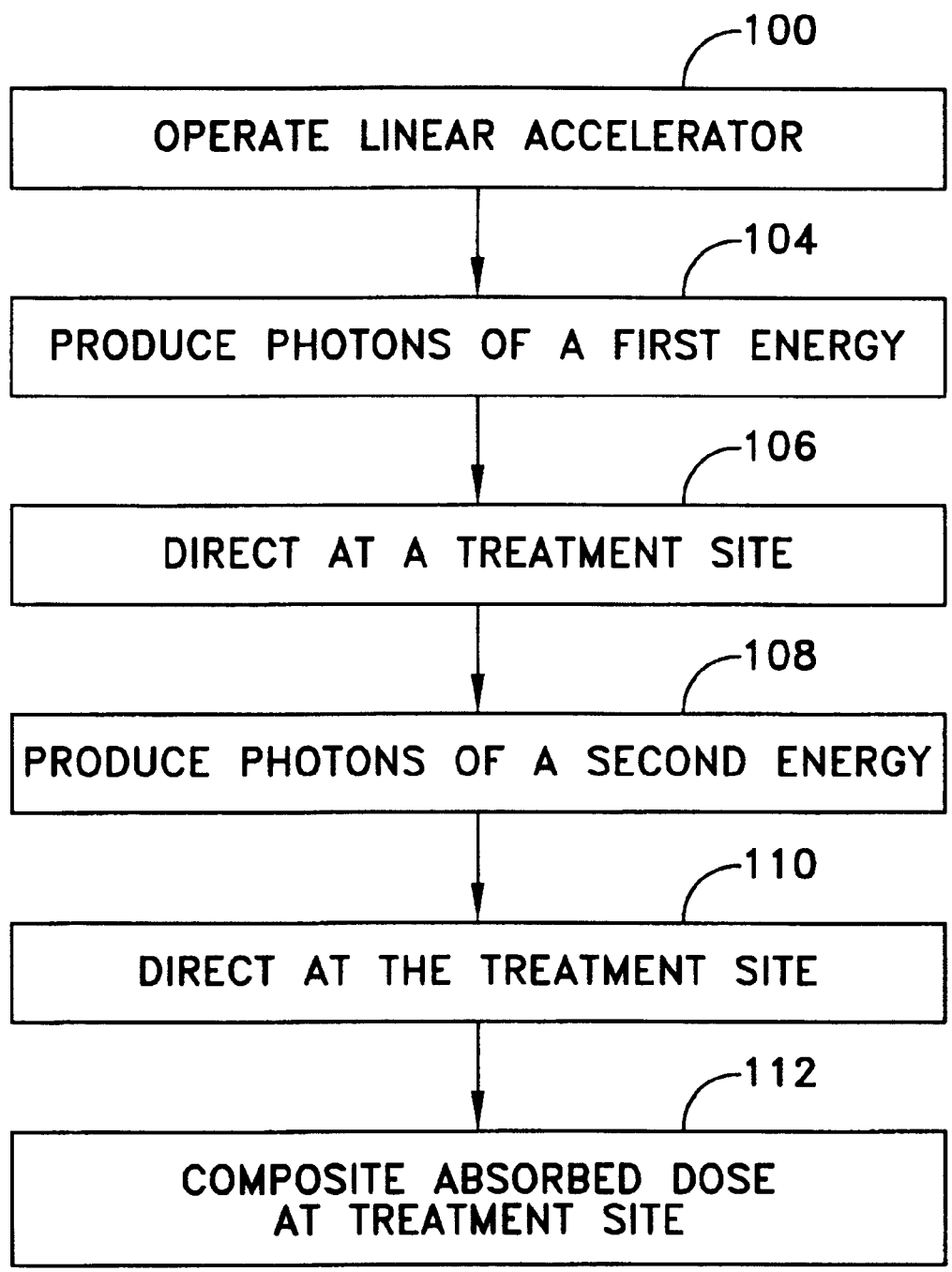
FIG. 2 is a flow diagram showing the steps of one embodiment of the present invention.

A portion of a radiotherapy system including radiation treatment device 2 is shown in FIG. 1. An electron beam 1 is generated in an electron accelerator 20. Accelerator 20 comprises an electron gun 21, a wave guide 22, and an evacuated envelope or guide magnet 23. A trigger system 3 generates injector trigger signals and supplies them to injector 5. Based on these injector trigger signals, injector 5 generates injector pulses which are fed to electron gun 21 in accelerator 20 for generating electron beam 1. Electron beam 1 is accelerated and guided by wave guide 22. For this purpose, a high frequency (HF) source (not shown) is provided which supplies radio frequency (RF) signals for the generation of an electromagnetic field supplied to wave guide 22. The electrons injected by injector 5 and emitted by electron gun 21 are accelerated by this electromagnetic field in wave guide 22 and exit at the end opposite to electron gun 21 as electron beam 1. Electron beam 1 then enters a bending magnet 23, and from there is guided through a window 7 along axis 10. The beam strikes a tungsten target 15, producing x-ray photons. The x-ray beam goes through a primary collimator and impinges on a flattening filter, whereby a uniform beam of radiation emerges. The beam goes through a passageway 51 of shielding blocks 50 and strikes a measuring chamber 60, in which the symmetry and flatness of the beam and the dose rate are ascertained.

An x-ray beam from linear accelerator 20 may be characterized by its associated "dmax", defined as the depth (usually measured from the surface of the skin) at which the x-ray beam's maximum energy dose is deposited, and also by the way it deposits its energy after dmax. An example of the relationship between beam energies and their associated dmax is listed in Table 1 below. It will be understood that these relationships will vary according to the make, model, manufacture, age, calibration, design, or tuning parameters, or other such known factors.

TABLE 1

| Beam Energy (MV) | dmax (10 × 10 cm field) |
| --- | --- |
| 6 | 1.5 cm ± 0.2 |
| 8 | 2.0 cm ± 0.2 |
| 10 | 2.3 cm ± 0.2 |

TABLE 1-continued

| Beam Energy (MV) | dmax (10 × 10 cm field) |
|---|---|
| 12 | 2.6 cm ± 0.2 |
| 15 | 2.9 cm ± 0.2 |

Referring to FIGS. 2–5, the present inventive method provides an effective absorbed dose, corresponding to a desired dmax at a treatment site, e.g., a tumor, that is of an intermediate energy value by mixing and matching the high and low energy photon beams produced by linear accelerator 20. Referring to the flow diagram of FIG. 2, one embodiment of the present invention includes the steps of operating a source of radiation 100, e.g., a dual energy version of linear accelerator 20; producing photons at a first energy 104; directing those photons at a treatment site 106 to impart a first absorbed dose. Linear accelerator 20 is then operated to produce photons at a second energy 108 that are directed at the treatment site 110 to impart a second absorbed dose. The appropriate selection of the first and second absorbed doses yields a composite or effective absorbed dose at the treatment site 112 equivalent to the dose produced by photons having an energy that is intermediate of the first and second energies.

The first and second absorbed doses may themselves be spaced apart in time and space, i.e., they do not need to be temporally sequential or directed at the same angle or direction relative to the treatment site. For example, the first and second absorbed doses could be seconds, minutes, hours, or even days apart without significantly effecting the method of the invention. The first and second absorbed doses could also be angularly spaced apart or directed at different portions of the treatment site without significantly effecting the method of the invention. The first and second absorbed doses could also be obtained according to the invention by substantially simultaneous application of photons of the first and the second energies. The first and second absorbed doses are selected by the treating physician and/or physicist on the basis of known methodologies for the efficacious application of radiation to diseased tissue.

The mixed beam energy, referred to as the "virtual energy (VE)", can be approximately determined by the following equation: Virtual Energy $\approx$x% (Low Energy)+y% (High Energy); where x+y$\approx$100%. In a general example, if sixty cGy is applied to a treatment site using a six MV beam, and then forty cGy is applied to that treatment site using a fifteen MV beam, so that in total, the tissue at the treatment site receives one hundred cGy, the dosage at the treatment site resembles the dmax achieved by application of an eight MV beam to the treatment site.

In another example, to deposit 100 cGy of radiation within a tumor according to the regimen associated with an eight MV beam, a first dosage is applied with a six MV beam and then a second dosage with a fifteen MV beam. The final result, i.e., the actual dosage at the tumor, being substantially similar to that given by an actual eight MV beam. Thus a regimen may be followed whereby a first beam representing 10% six MV and a second beam representing 90% fifteen MV yields a dmax at the treatment site that is substantially similar to a beam of 100% twelve MV photons. Or, a regimen whereby a first beam representing 20% six MV and a second beam representing 80% fifteen MV yields a dmax at the treatment site that is substantially similar to a beam of 100% ten MV, and so on. Thus by varying the dose given by six and fifteen MV beams, a beam can be produced having an intermediate dmax at a treatment site. Advantageously, the present inventive method may be practiced by appropriately programming and fine tuning a conventional dual energy linear accelerator having a special or general purpose computer associated with it. The absorbed dose associated with non-integer photon energies may also be simulated, e.g., 4.5 or 8.9 MV photons, with the method of the invention and existing dual beam linear accelerators, by simply adjusting the ratio of the first energy beam to the second energy beam.

In a more specific example, a two-hundred cGy absorbed dose may be delivered to a depth of 3 cm, approximating an eight MV beam and a field size of 10-by-10 cm, in the following manner. A six MV beam is combined with a fifteen MV beam in a 4:1 ratio to yield a combined isodose distribution of eight MV. More particularly, to deliver two-hundred cGy to a 3 cm depth, a first absorbed dose of one-hundred-sixty cGy is imparted to the treatment site with a six MV beam and then a second absorbed dose of forty cGy is imparted to the treatment site with a fifteen MV beam. Such absorbed dosages are delivered to the treatment site in terms of "monitor units" or "MU's", where one MU is equal to one cGY at 1.5 cm depth for a 10-by-10 cm field size using a six MV beam, and one MU equal to one cGY at 3 cm depth for a 10-by-10 cm field size using a fifteen MV beam. Thus to deliver one-hundred and sixty cGy to 3 cm depth with a six MV beam, a one-hundred-sixty-seven MU must be delivered to the treatment site. It will be understood that at a 3 cm depth in soft tissue, a six MV photon beam's intensity is decreased to 96% of its maximum, thus the dosage must be increased by an amount to off-set this reduction, here the off-set is seven MU. For a fifteen MV beam, an MU of forty may be used since for a fifteen MV beam one MU is equal to one cGy at 3 cm depth and a 10-by-10 cm field size. Thus by delivering an effective one-hundred sixty cGy to a 3 cm depth with a six MV beam and then forty cGy with a fifteen MV beam, 200 cGy is delivered to 3 cm depth, and the composite absorbed dose distribution imparted by this mixing of beams and energies yields a substantially similar absorbed dosage as would have been the case if an eight MV beam had been applied to the treatment site. In this way, by mixing the percentage of radiation provided by a low energy beam and a high energy beam, the beam profile of all intermediate energies, i.e., between the low and high energies applied, can be effectively mimicked.

The following table provides representative, nonlimiting examples of a one hundred cGy dosage obtained by various combinations of percentages of six MV and fifteen MV photons. The ratio of beam energies may also be adjusted fractionally in accordance with the broad scope of the invention, to obtain both integer and noninteger values for the composite absorbed dose at the treatment site.

TABLE 2

| cGy by 6 MV | cGy by 15 MV | Virtual Energy (equivalent to 100 cGy by the VE) |
|---|---|---|
| 0 | 100 | 15 MV |
| 10 | 90 | 12 MV |
| 20 | 80 | 10 MV |
| 40 | 60 | 9 MV |
| 60 | 40 | 8 MV |
| 100 | 0 | 6 MV |

The above virtual energy equivalent beams produced by the present method have been compared with an actual beam's characteristics, such as dmax, 80% depth (i.e., at a depth from the surface where the beam deposits 80% of the radiation dose as compared to dmax) and Pdd (percent depth dose) at 10 cm. The following table presents the dmax for actual energy beams generated in single (or dual) energy linear accelerators (Real or Nominal MV) and virtual energy beam profiles provided by operating those single (or dual) energy linear accelerators according to the method of the present invention.

TABLE 3

| Desirable Energy | dmax by Real MV Energy | dmax by Virtual Energy |
| --- | --- | --- |
| 15 MV | 2.9 cm ± 0.2 | 3.0 cm ± 0.2 |
| 12 MV | 2.6 cm ± 0.2 | 2.8 cm ± 0.2 |
| 10 MV | 2.3 cm ± 0.2 | 2.5 cm ± 0.2 |
| 8 MV | 2.0 cm ± 0.2 | 2.2 cm ± 0.2 |
| 6 MV | 1.5 cm ± 0.2 | 1.5 cm ± 0.2 |

The next table is representative of a depth from the surface where the beam deposits 80% of the radiation as compared to dmax provided by operating a single (or dual) energy linear accelerator according to the method of the present invention.

TABLE 4

| Desirable Energy | 80% depth Real MV Energy | 80% depth Virtual Energy |
| --- | --- | --- |
| 15 MV | 9.1 cm ± 0.2 | 9.1 cm ± 0.2 |
| 12 MV | 8.5 cm ± 0.2 | 8.6 cm ± 0.2 |
| 10 MV | 8.0 cm ± 0.2 | 8.4 cm ± 0.2 |
| 8 MV | 7.5 cm ± 0.2 | 7.7 cm ± 0.2 |
| 6 MV | 6.7 cm ± 0.2 | 6.5 cm ± 0.2 |

The next table is representative of the percent depth dose at 10 cm, i.e., the percent of radiation deposited at 10 cm as compared to dmax provided by operating a single (or dual) energy linear accelerator according to the method of the present invention.

TABLE 5

| Desirable Energy | Pdd at 10 cm Real MV Energy | Pdd at 10 cm Virtual Energy |
| --- | --- | --- |
| 15 MV | 77% ± 2% | 76.4% ± 2% |
| 12 MV | 75% ± 2% | 75% ± 2% |
| 10 MV | 73% ± 2% | 74% ± 2% |
| 8 MV | 71% ± 2% | 70% ± 2% |
| 6 MV | 67% ± 2% | 67% ± 2% |

Thus, looking at the three criteria: dmax, 80% depth, and Pdd at 10 cm, the virtual energy beam profile created by operating any linear accelerator according to the method of the present invention closely mimics that of real megavoltage beam profiles.

Figure 6:
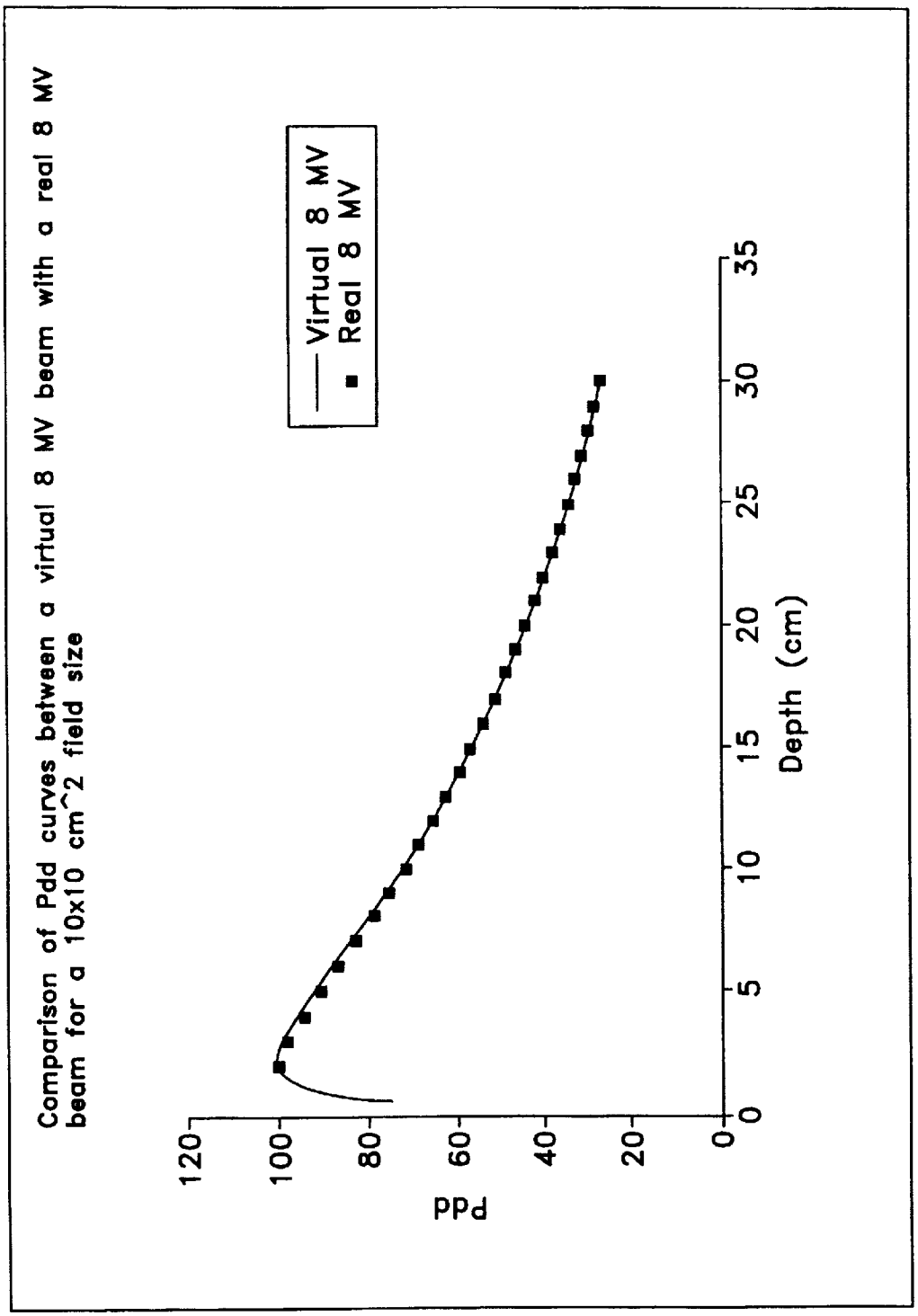
FIG. 6, is a graphical representation of actual test data comparing the Pdd at various depths of a virtual energy 8MV beam, for a 10×10 cm field, with an actual 8MV beam at various depths, for a 10×10 cm field.

Referring to FIG. 6, the Pdd at various depths of a virtual energy 8 MV beam, for a 10×10 cm field, was compared to that of an actual 8 MV beam. Here the virtual energy 8 MV is produced by mixing a 6 MV and 15 MV beam as described in Table 2.

The radiation oncology staff can program the linear accelerator to obtain virtual energy of say seven or eight MV and give a course of treatment that would mimic a course of treatment that is given by a real photon beam of seven or eight MV. Thus, a four MV and fifteen MV dual energy linear accelerator may be operated according to the method to yield a nearly continuous range of energies, e.g., 4, 5, 6, 7, 8, 9, 10, 11, 12, 13, 14, or 15 MV photons.

Figure 3:
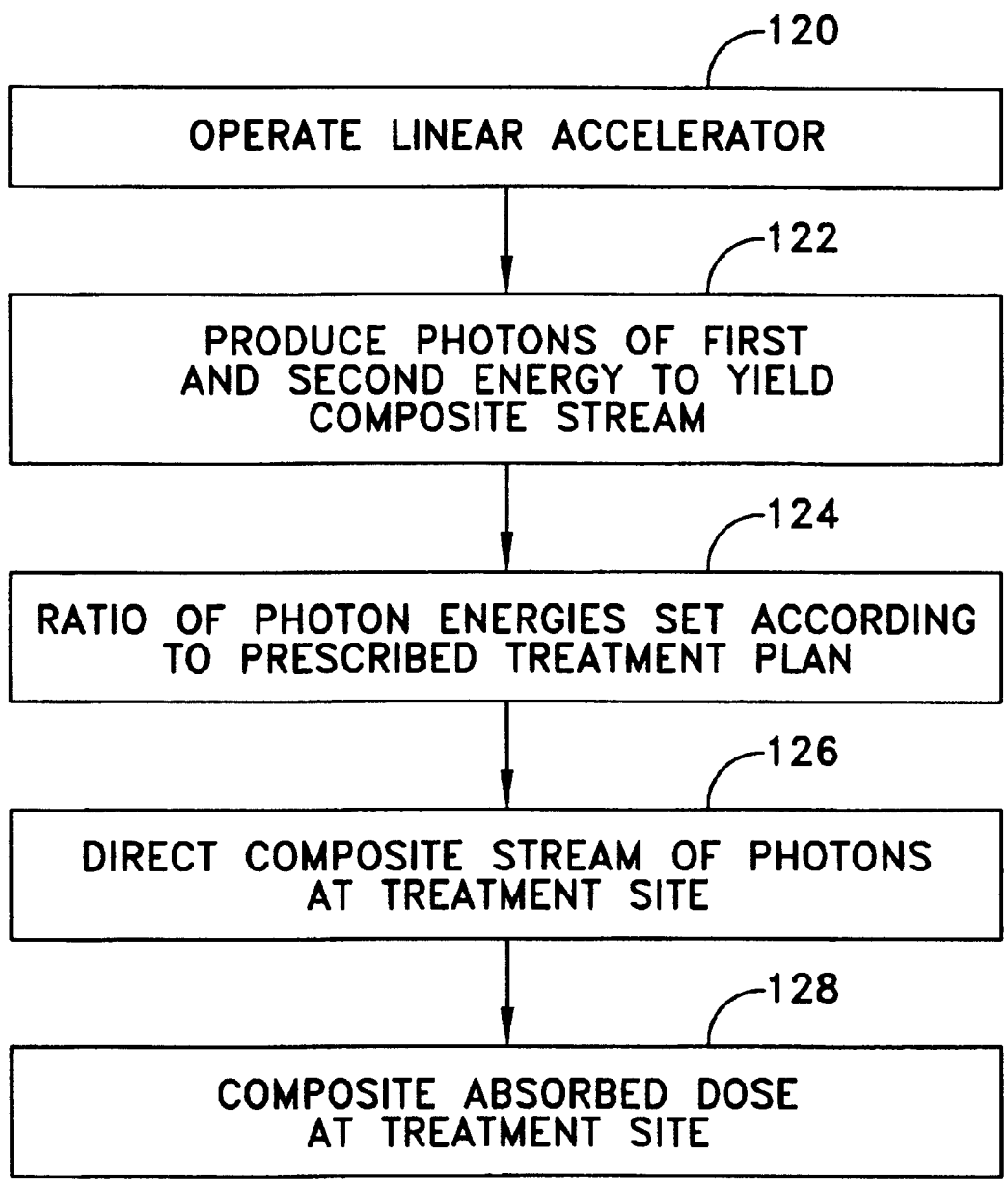
FIG. 3 is a flow diagram showing the steps of another embodiment of the present invention.

Referring to FIG. 3, in an alternative embodiment a dual energy linear accelerator is operated 120 to produce simultaneously photons at a first energy and photons at a second energy 122 where the ratio of first energy photons to second energy photons is set according to a prescribed treatment plan 124. This composite stream of photons is then directed at a treatment site 126. The appropriate selection of the ratio of first energy photons to second energy photons yields an absorbed dose at the treatment site 128 equivalent to the dose produced by photons having an energy that is intermediate of the first and second energies. By way of example only, two identical fields may be set up in a treatment planning system, with one of the fields treated by to six MV and the other treated by fifteen MV with relative weightings of 4:1. These same two fields may then be exported to a record-and-verify system (identified generally by reference 75 in FIG. 1) which then commands linear accelerator 20 to execute the dose delivery. Of course, it will be understood that other relative weightings and ratios of beam energies are possible with this or other embodiments of the present invention.

Figure 4:
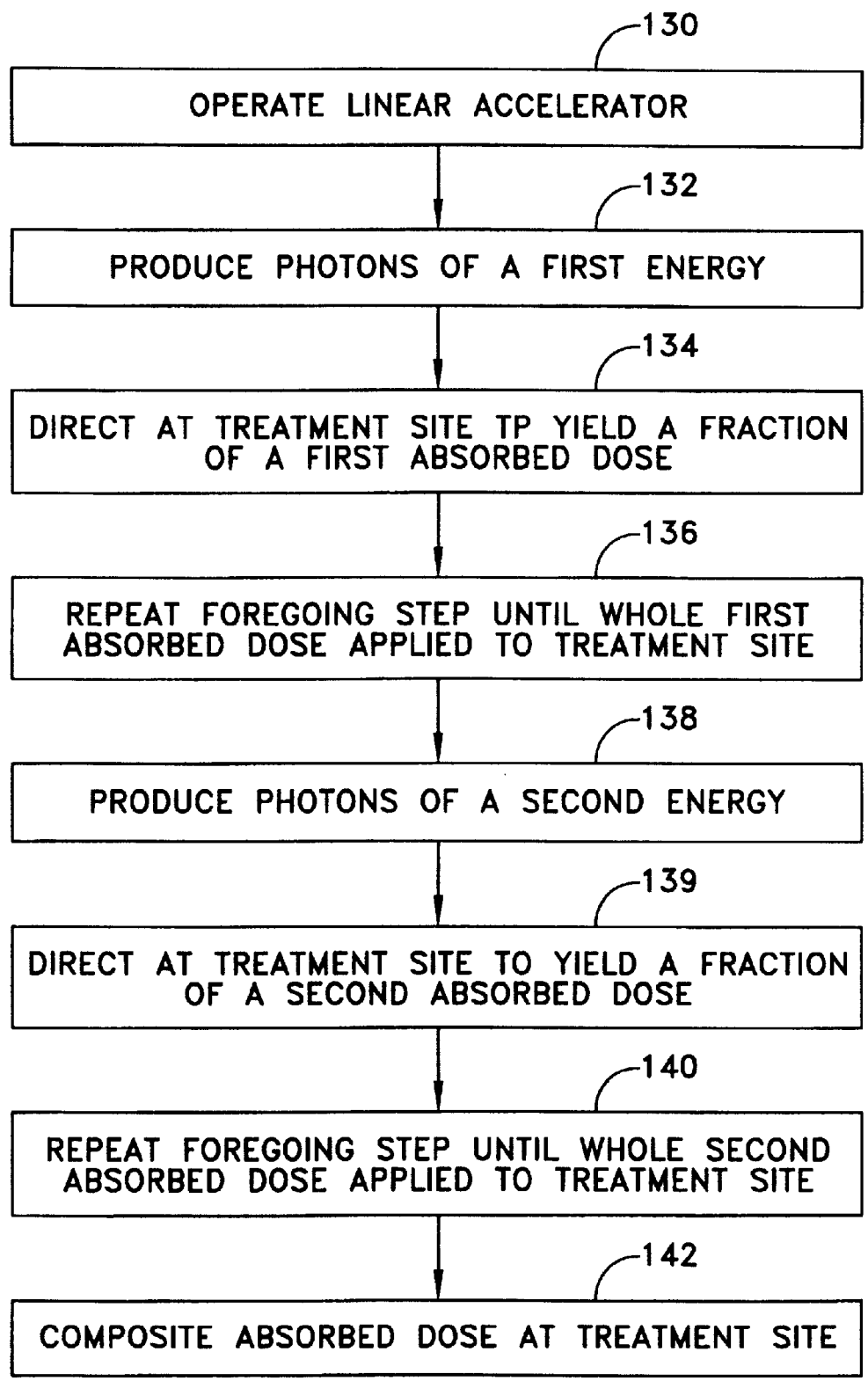
FIG. 4 is a flow diagram showing the steps of yet another embodiment of the present invention.

Referring to FIG. 4, in another embodiment of the invention a six MV beam is applied in one treatment plan and a fifteen MV beam is applied in a second treatment plan, with each treatment plan delivering its respective dose so as to achieve a two-hundred cGy absorbed dose at the treatment site, i.e., the six MV plan imparting one-hundred sixty cGy and the fifteen MV plan imparting forty cGy. Each treatment plan may be exported separately to record-and-verify system 75, which then commands linear accelerator 20 to deliver the dose. Thus the steps of this embodiment comprise operating a dual energy linear accelerator 130 so as to produce photons at a first energy 132; directing the first energy photons at a treatment site to impart a fraction of a first absorbed dose 134; repeating the foregoing step until a whole first absorbed dose has been applied to the treatment site 136; operating the dual energy linear accelerator so as to produce photons at a second energy 138; directing the second energy photons at the treatment site to impart a fraction of a second absorbed dose 139; and repeating the foregoing step until a whole second absorbed dose has been applied to the treatment site 140, wherein the first and second whole absorbed doses are selected so as to impart an effective absorbed dose at the treatment site equivalent to an absorbed dose produced by photons having an energy that is intermediate of the first and second energies 142.

For example, if the total absorbed dose for the treatment is four-thousand cGy. With a 4:1 ratio, the six MV beam can be set to deliver 3200 cGy and the fifteen MV beam can be set to deliver eight-hundred cGy. Thus the mixed beam result can be effected by delivering all three-thousand two-hundred cGy with the six MV beam in (3200/200 or 16) fractions, followed by four fractions of fifteen MV beam at two-hundred cGy each, or vice versa, or in any other combinations that will result in a final absorbed dose of three-thousand two-hundred cGy of six MV and eight-hundred cGy of fifteen MV. Of course, it will be understood that other relative weightings and ratios of beam energies are possible with this or other embodiments of the present invention.

Figure 5:
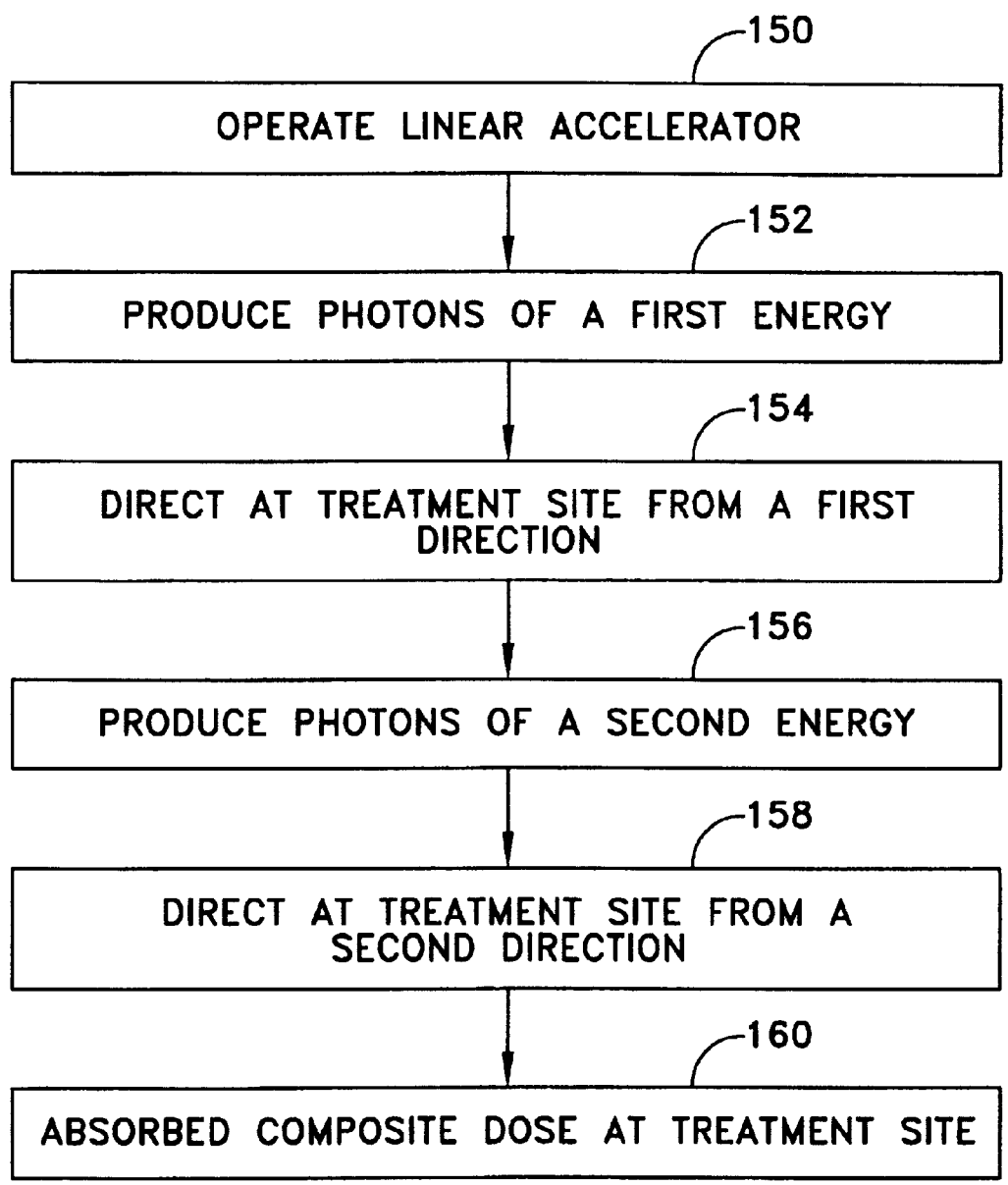
FIG. 5 is a flow diagram showing the steps of a further embodiment of the present invention.

Referring to FIG. 5, with an inverse planning algorithm or other dose optimization algorithms, it is also possible for an optimal treatment plan to consist of mixed photon energies in various fashions, either in the same direction (same gantry angle) or at different gantry angles. For example, a two-hundred cGy may be imparted to a depth of three cm, with the user setting all optimization requirements. An inverse planning algorithm may be implemented to generate an intensity map with a combination of rotation arcs, with a combination of beam energies, for example, six MV in the first arc, fifteen MV in the second arc and then six MV again in a third arc. This arrangement however may not deliver an eight MV beam because the inverse planning algorithm produces an optimal distribution based on the user's specification. Although the combined distribution may not be substantially the same as that of an eight MV beam, it is nonetheless the result of mixing photon beams in different proportions. In the dose delivery state, linear accelerator 20 delivers the combination of arcs with the associated MU's. Thus the steps of this embodiment comprise operating a dual energy linear accelerator 150 so as to produce photons at a first energy 152; directing the first energy photons at a treatment site from a first direction to impart a first absorbed dose 154; operating the dual energy linear accelerator so as to produce photons at a second energy 156; and directing the second energy photons at the treatment site from a second direction 158 to impart a second absorbed dose wherein the first and second absorbed doses are selected so as to yield an effective absorbed dose at the treatment site 160 equivalent to an absorbed dose produced by photons having an energy that is intermediate of the first and second energies.

It is to be understood that the present invention is by no means limited only to the particular constructions herein disclosed and shown in the drawings, but also comprises any modifications or equivalents within the scope of the claims.

What is claimed is:

1. A method for producing a broad range of therapeutic radiation energy levels from a source of more than one therapeutic radiation comprising:
   (A) operating said source of therapeutic radiation so as to produce radiation at a first energy;
   (B) directing said first energy radiation at a treatment site to impart a first absorbed dose;
   (C) operating said source of therapeutic radiation so as to produce radiation at a second energy; and
   (D) directing said second energy radiation at said treatment site to impart a second absorbed dose wherein said first and second absorbed doses are selected so as to yield an effective absorbed dose at said treatment site equivalent to an absorbed dose produced by radiation having an energy that is intermediate of said first and second energies.

2. A method for producing a broad range of therapeutic radiation energy levels with a dual energy linear accelerator comprising:
   (A) operating a dual energy linear accelerator so as to produce photons at a first energy;
   (B) directing said first energy photons at a treatment site to impart a first absorbed dose;
   (C) operating said dual energy linear accelerator so as to produce photons at a second energy;
   (D) directing said second energy photons at said treatment site to impart a second absorbed dose wherein said first and second absorbed doses are selected so as to yield an effective absorbed dose at said treatment site equivalent to an absorbed dose produced by photons having an energy that is intermediate of said first and second energies.
   (E) directing said second energy radiation at said treatment site to impart a second absorbed dose wherein said first and second absorbed doses are selected to yield an effective absorbed dose characteristics (distributions) at said treatment site equivalent to an absorbed dose produced by radiation having an energy that is intermediate of said and second energies.

3. The method according to claim 2 wherein said steps (B) and (C) are temporally sequential.

4. The method according to claim 2 wherein said steps (B) and (C) are spatially sequential relative to said treatment site.

5. The method according to claim 2 wherein said dual energy linear accelerator is operated so as to produce photons having an energy in the range of approximately four to six megavolts and corresponding to said first energy.

6. The method according to claim 2 wherein said dual energy linear accelerator is operated so as to produce photons having an energy of approximately fifteen megavolts and corresponding to said second energy.

7. The method according to claim 2 wherein said dual energy linear accelerator is operated so as to produce photons having an energy in the range of approximately four to six megavolts and corresponding to said second energy.

8. The method according to claim 2 wherein said dual energy linear accelerator is operated so as to produce photons having an energy of approximately fifteen megavolts and corresponding to said first energy.

9. The method according to claim 2 wherein said effective absorbed dose at said treatment site comprises a fractional value.

10. The method according to claim 2 wherein said first energy is lower than said second energy.

11. A method for producing a broad range of therapeutic radiation energy levels with a dual energy linear accelerator comprising:
    (A) operating a dual energy linear accelerator so as to produce simultaneously photons at a first energy and photons at a second energy so as to create a composite stream of photons where the ratio of said first energy photons to said second energy photons is set according to a proportion dependent upon a required therapeutic absorbed dose; and
    (B) directing said composite stream of photons at a treatment site whereby an absorbed dose at said treatment site is equivalent to the dose produced by photons having an energy that is intermediate of said first and said second energies.

12. The method according to claim 11 wherein said photons are spatially sequential relative to said treatment site.

13. The method according to claim 11 wherein said dual energy linear accelerator is operated so as to produce photons having an energy of approximately six megavolts and corresponding to said first energy.

14. The method according to claim 11 wherein said dual energy linear accelerator is operated so as to produce photons having an energy of approximately fifteen megavolts and corresponding to said second energy.

15. The method according to claim 11 wherein said dual energy linear accelerator is operated so as to produce photons having an energy of approximately six megavolts and corresponding to said second energy.

16. The method according to claim 11 wherein said dual energy linear accelerator is operated so as to produce photons having an energy of approximately fifteen megavolts and corresponding to said first energy.

17. The method according to claim 11 wherein said effective absorbed dose at said treatment site corresponds to an absorbed dose effected by a noninteger energy photon.

18. A method for producing a broad range of therapeutic radiation energy levels with a dual energy linear accelerator comprising:
- (A) operating a dual energy linear accelerator so as to produce photons at a first energy;
- (B) directing said first energy photons at a treatment site to impart a fraction of a first absorbed dose;
- (C) repeating step (B) until a whole first absorbed dose has been applied to said treatment site;
- (D) operating said dual energy linear accelerator so as to produce photons at a second energy;
- (E) directing said second energy photons at said treatment site to impart a fraction of a second absorbed dose; and
- (F) repeating step (E) until a whole second absorbed dose has been applied to said treatment site wherein said first and second whole absorbed doses are selected so as to yield an effective absorbed dose at said treatment site equivalent to an absorbed dose produced by photons having an energy that is intermediate of said first and second energies.

19. The method according to claim 18 wherein said steps (B) through (F) are temporally sequential.

20. The method according to claim 18 wherein said steps (B) and (E) are spatially sequential relative to said treatment site.

21. The method according to claim 18 wherein said effective absorbed dose at said treatment site corresponds to an absorbed dose effected by a noninteger energy photon.

22. A method for producing a broad range of therapeutic radiation energy levels with a dual energy linear accelerator comprising:
- (A) operating a dual energy linear accelerator so as to produce photons at a first energy;
- (B) directing said first energy photons at a treatment site from a first direction to impart a first absorbed dose;
- (C) operating said dual energy linear accelerator so as to produce photons at a second energy; and
- (D) directing said second energy photons at said treatment site from a second direction to impart a second absorbed dose wherein said first and second absorbed doses are selected so as to yield an effective absorbed dose at said treatment site equivalent to an absorbed dose produced by photons having an energy that is intermediate of said first and second energies.

23. The method according to claim 22 wherein said step (B) comprises: directing said first energy photons at a treatment site by rotation relative to said treatment site to yield a first absorbed dose.

24. The method according to claim 22 wherein said step (D) comprises:
    directing said second energy photons at said treatment site by rotation relative to said treatment site to yield a second absorbed dose wherein said first and second absorbed doses are selected so as to yield an effective absorbed dose at said treatment site equivalent to an absorbed dose produced by photons having an energy that is intermediate of said first and second energies.

25. The method according to claim 22 wherein said steps (B) and (D) comprise:
    directing said first energy photons at a treatment site by rotation relative to said treatment site to impart a first absorbed dose; and
    directing said second energy photons at said treatment site by rotation relative to said treatment site to impart a second absorbed dose wherein said first and second absorbed doses are selected so as to yield an effective absorbed dose at said treatment site equivalent to an absorbed dose produced by photons having an energy that is intermediate of said first and second energies.

26. The method according to claim 24 wherein step (A) comprises:
    generating an intensity map with a combination of rotation arcs and a combination of beam energies and operating a dual energy linear accelerator so as to yield an effective absorbed dose.

* * * * *